United States Patent
Xu et al.

(10) Patent No.: US 12,403,472 B2
(45) Date of Patent: Sep. 2, 2025

(54) METHOD FOR FORMING AND RESPECTIVELY EXPORTING DROPLET WRAPPING SINGLE PARTICLE IN MICRO-FLUIDIC CHIP

(71) Applicant: QINGDAO INSTITUTE OF BIOENERGY AND BIOPROCESS TECHNOLOGY, CHINESE ACADEMY OF SCIENCES, Shandong (CN)

(72) Inventors: Teng Xu, Shandong (CN); Bo Ma, Shandong (CN); Jian Xu, Shandong (CN)

(73) Assignee: QINGDAO INSTITUTE OF BIOENERGY AND BIOPROCESS TECHNOLOGY, CHINESE ACADEMY OF SCIENCES, Shandong (CN)

( * ) Notice: Subject to any disclaimer, the term of this patent is extended or adjusted under 35 U.S.C. 154(b) by 346 days.

(21) Appl. No.: 16/764,803

(22) PCT Filed: Nov. 9, 2018

(86) PCT No.: PCT/CN2018/114807
§ 371 (c)(1),
(2) Date: May 15, 2020

(87) PCT Pub. No.: WO2019/096070
PCT Pub. Date: May 23, 2019

(65) Prior Publication Data
US 2020/0376490 A1 Dec. 3, 2020

(30) Foreign Application Priority Data
Nov. 15, 2017 (CN) .......................... 201711130429.2

(51) Int. Cl.
*B01L 3/00* (2006.01)

(52) U.S. Cl.
CPC ... *B01L 3/502761* (2013.01); *B01L 3/502715* (2013.01); *B01L 2200/0652* (2013.01);
(Continued)

(58) Field of Classification Search
CPC ......... B01L 3/502761; B01L 3/502715; B01L 2200/0652; B01L 2300/08;
(Continued)

(56) References Cited

U.S. PATENT DOCUMENTS 6,635,226 B1 10/2003 Tso et al.
2003/0096405 A1* 5/2003 Takayama ............. F04B 19/006
435/366
(Continued)

FOREIGN PATENT DOCUMENTS

CN 103831140 A 6/2014
CN 105259163 A 1/2016
(Continued)

OTHER PUBLICATIONS

International Search Report and Written Opinion (in English and Chinese) issued in PCT/CN2018/114807, dated Jan. 31, 2019, 12 pages provided.
(Continued)

*Primary Examiner* — Matthew D Krcha
(74) *Attorney, Agent, or Firm* — HSML P.C.

(57) ABSTRACT

A micro-fluidic chip that can be used for screening a single particle and forming and exporting a droplet wrapping same. The micro-fluidic chip is connected to a liquid sample introduction apparatus, and can constitute a micro-fluidic chip apparatus for forming a droplet for wrapping a single particle. The micro-fluidic chip apparatus can further constitute, with a particle capture apparatus, a micro-fluidic operating system for forming a droplet wrapping a single particle. Further provided is a method for forming and
(Continued)

respectively exporting a droplet wrapping a single particle in a micro-fluidic chip.

2 Claims, 3 Drawing Sheets

(52) U.S. Cl.
CPC ... *B01L 2300/08* (2013.01); *B01L 2400/0406* (2013.01); *B01L 2400/043* (2013.01); *B01L 2400/0457* (2013.01)

(58) Field of Classification Search
CPC ....... B01L 2400/0406; B01L 2400/043; B01L 2400/0457; B01L 2200/027; B01L 2200/0668; B01L 2200/0673; B01L 2300/0816; B01L 2300/0883; B01L 2300/0887; B01L 2300/165; B01L 2400/0454; B01L 3/502707; C12M 47/04
See application file for complete search history.

(56) References Cited

U.S. PATENT DOCUMENTS

| | | | | |
|---|---|---|---|---|
| 2004/0229349 | A1* | 11/2004 | Daridon | C12M 21/06 |
| | | | | 435/305.2 |
| 2009/0014360 | A1* | 1/2009 | Toner | B01D 45/12 |
| | | | | 209/208 |

FOREIGN PATENT DOCUMENTS

| | | | | |
|---|---|---|---|---|
| CN | 205103262 U | 3/2016 | | |
| CN | 205379906 U | 7/2016 | | |
| EP | 2514528 A1 | 10/2012 | | |
| WO | 2008082432 A1 | 7/2008 | | |
| WO | 2008130977 A2 | 10/2008 | | |
| WO | WO-2014165559 A2 * | 10/2014 | ........ | B01L 3/502784 |
| WO | WO-2015084458 A2 * | 6/2015 | .......... | B01L 3/50273 |

OTHER PUBLICATIONS

Communication issued in European Application No. 18880018.9, dated Mar. 1, 2021.
Communication issued in European Application No. 18880018.9, dated Apr. 24, 2023.
The European search report issued in European Application No. 18880018.9, dated Dec. 3, 2020.

* cited by examiner

METHOD FOR FORMING AND RESPECTIVELY EXPORTING DROPLET WRAPPING SINGLE PARTICLE IN MICRO-FLUIDIC CHIP

TECHNICAL FIELD

This invention relates to the technical field of microfluidics, in particular to a method for forming and exporting single microparticle-encapsulated droplets by utilizing microfluidic chips, which can be used for such fields as single-cell sorting, single-cell isolation, single-cell sequencing, single-cell morphology analysis, single-cell culture, drug screening, etc.

BACKGROUND OF THE INVENTION

As we all know, cell diversity exists in various cell populations, such as bacteria, yeast, mammalian cells, and so on. Even for the daughter cells divided from the same mother cell, there are differences among individual cells. Single-cell analysis refers to the study of differences among individual cells in cell populations, including cell size, growth rate, chemical composition (phospholipids, proteins, metabolites, DNA/RNA) and the like, and the study of the reason and mechanism of those differences. The research content relates to the fields of tumor biology, stem cells, microbiology, neurology, immunology, etc.

The biggest challenge in single-cell analysis lies in the small cell size and the complex chemical composition and trace components caused by the small size. The size of a single cell is mostly distributed on the micrometer scale, under which extremely high requirements were placed on the manipulation and analysis of single cells, and the accuracy and sensitivity of the instruments. Therefore, to achieve single-cell analysis, two problems should be solved firstly. One is the single-cell capture, isolation and extraction; and the other is single-cell signal acquisition.

With the development of fluorescence microscopy, single-cell Raman, electrochemical technology, mass spectrometry, and the development of qPCR technology in the past years, multiple analysis of single-cell components has been achieved. However, progress in single-cell capture, isolation and extraction has been slow. At present, methods using microfluidic chip technology can be roughly divided into two parts: single-cell array capture and flow cytometry. The array capture method can achieve the real-time monitoring of single cells, and it is convenient to change the experimental conditions for study of the influences of different culture conditions on single cells, but the throughput is low. Flow cytometry is usually based on the single-cell droplet encapsulation technology, which has the advantages of high detection throughput and convenient cell isolation. However, due to the short detection time, it is generally difficult to obtain more detailed information of a single cell. Currently, fluorescence flow cytometry is more commonly used. However, how to separate and remove the cells analyzed and selected by the microfluidic chip analysis and then perform downstream analysis remains difficult currently. For example, in single-cell gene profiling and sequencing, it is necessary to transfer a target cell from a capture array or chip into a test tube, avoiding cell damage and pollution from the external environment during the transfer process.

BRIEF SUMMARY OF THE INVENTION

The object of the present invention is to provide a technology for separating and exporting a single target microparticle. And the present invention achieves the detection and capture of a single target microparticle in a microfluidic chip, and the transfer from the microfluidic chip to an external test tube.

The "microparticles" as used in the present invention refer to particles that can be suspended in a non-organic phase solution (such as an aqueous phase) and pass through the microfluidic chip of the present invention, including particles of biological origin and non-biological origin, for example, eukaryotic cells, prokaryotic cells, single cell organisms, viral particles, organelles, particles formed by biological macromolecules, drug particles, drug carrier particles, liposomes, polymer particles, and so on.

In a first aspect of the present invention, it provides a microfluidic chip, wherein the microfluidic chip comprises a cover layer and a substrate layer; wherein the substrate layer comprises at least one sample channel, and the sample channel comprises a microfluidic channel and a detection cell (5); and the cover layer comprises a sample injection hole (1) and an oil storage well hole (6); wherein the oil storage well hole (6) and the substrate layer form an oil storage well; the inlet (7) of the sample channel is connected with the sample injection hole (1), and the outlet (8) of the sample channel is connected with the oil storage well.

In another preferred embodiment, the material of the cover layer is selected from, but not limited to, quartz, PDMS (polydimethylsiloxane), PMMA (polymethyl methacrylate), borosilicate glass, calcium fluoride, and the material of the substrate layer is selected from, but not limited to, quartz, PDMS, PMMA, borosilicate glass, and calcium fluoride.

In another preferred embodiment, the surface of the oil storage well is a hydrophobic and lipophilic surface.

In another preferred embodiment, the sample injection hole (1) is in connection with a sampling injection catheter interface.

In another preferred embodiment, the microfluidic channel comprises a straight channel (2) and at least one curved channel (3). The curved channel according to the present invention refers to a microfluidic channel that is not linear.

In a preferred embodiment, the width of the microfluidic channel is 30-300 μm, and the height is 15-50 μm.

In another preferred embodiment, the detection cell (5) and the oil storage well hole (6) are connected through a channel (23), and the channel (23) is a straight channel.

In another preferred embodiment, the sample channel further comprises at least one liquid storage well (4), preferably, in another preferred embodiment, the capacity of the detection cell (5) is smaller than that of the liquid storage well (4).

In another preferred embodiment, the detection cell (5) is located between the liquid storage well (4) and the oil storage well hole (6), and the liquid storage well (4) and the detection cell (5) are connected through a channel (22), and the liquid storage well (4) and the curved channel (3) are connected through a channel (21), wherein the channels (21, 22) comprise at least one straight channel or at least one curved channel.

The detection cell according to the present invention can be used for collecting characteristic signals of microparticles or capturing individual microparticles; and the liquid storage well according to the present invention is used for storing liquid to be tested.

In another preferred embodiment, the width of the channel (22) is smaller than that of the channel (21);

In another preferred embodiment, the width of the channel (23) is smaller than that of the channel (22);

In another preferred embodiment, the width of the channel (21) is 200-300 μm; preferably 200 μm;

In another preferred embodiment, the width of the channel (22) is 45-230 μm; preferably 100 μm;

In another preferred embodiment, the width of the channel (23) is 30-100 μm; preferably 45 μm;

In another preferred embodiment, the height of the sample channel is 15-50 μm.

In another aspect of the present invention, it provides a method for preparing the microfluidic chip, wherein the method includes steps: (i) etching the substrate layer according to the design of the sample channel, (ii) punching the sample injection holes and oil storage well holes on the cover layer, (iii) aligning the cover layer and the substrate layer and bonding the same using low-temperature bonding method, and (iv) hydrophobization of the surfaces. In a preferred embodiment, the height of the sample channel is 15-50 μm.

In another aspect of the present invention, it provides a microfluidic chip device for forming single microparticle-encapsulated liquid droplets, wherein the device comprises a microfluidic chip provided in present invention and a liquid sample injection device, wherein the liquid sample injection device is connected with the sample injection hole (1), and the liquid sample injection device is selected from, but not limited to, a gravity-driven sample injection device, a syringe, a peristaltic pump, and/or a syringe pump.

In a preferred embodiment, the gravity-driven sample injection device includes a height-adjustable sample holder, a sample container, and a catheter, wherein the sample container, capable of moving up and down on the height-adjustable sample holder, is connected with the sample injection hole (1) through the catheter.

In another preferred embodiment, the sample container moving mode is by manual adjustment.

In another preferred embodiment, the sample container moving mode is by electrical adjustment.

In another preferred embodiment, the height-adjustable sample holder is designed on a slide rail, and the slide rail has an electrically movable slider for fixing a sample container; more preferably, the height-adjustable sample holder further includes a height adjusting controller that controls the slider to move up and down on the slide rail.

In another aspect of the present invention, it provides a microfluidic operating system for forming single microparticle-encapsulated droplets, wherein the system comprises the microfluidic chip or the microfluidic chip device provided by the present invention, and a microparticle capture device, wherein the microparticle capture device is selected from optical tweezers and magnetic tweezers.

The optical tweezers and magnetic tweezers used in the present invention are the prior arts in this field.

The capture in the present invention refers to that the target microparticles are fixed by a microparticle capture device including optical tweezers and magnetic tweezers, so that the target microparticles do not move with the chip when the microfluidic chip of the present invention is moved.

In another preferred embodiment, the microfluidic operating system further includes a sample detection device, wherein the sample detection device includes, but is not limited to, a Raman detection device, an optical microscope, and a fluorescence microscope.

In another preferred embodiment, the microfluidic operating system further includes a device for exporting single microparticle-encapsulated droplets, wherein the device for exporting single microparticle-encapsulated droplets is selected from a capillary tube and a pipette tip.

In another aspect of the present invention, it provides a method for forming and exporting single microparticle-encapsulated droplets, wherein the method utilizes the microfluidic chip or the microfluidic chip device or the microfluidic operating system provided by the present invention, and includes steps: (i) injecting an oil phase into the oil storage well; (ii) injecting the microparticle phase solution into the sample channel of the microfluidic chip through the injection hole; (iii) adjusting the liquid flow in the sample channel so that the interface between the microparticle phase and the oil phase in the oil storage well is steadily stationary nearby the outlet (8) of the sample channel; (iv) capturing the target microparticles with a microparticle capture device, moving the microfluidic chip, and dragging the target microparticles to the vicinity of the interface between the aqueous phase and oil phase; (v) adjusting the liquid flow in the sample channel to allow the target microparticles to enter the oil storage well and to form liquid droplets encapsulating single target microparticles; and (vi) exporting the droplets encapsulating a single target microparticle; wherein the method for adjusting the liquid flow in the sample channel is selected from, but not limited to, gravity-driven adjusting, injection pump-driven adjusting, and peristaltic pump-driven adjusting.

In a preferred embodiment, the microparticle capturing device captures target microparticles from the detection cell.

In another preferred embodiment, the oil phase is selected from mineral oil, silicone oil, fluorocarbon oil, vegetable oil, and petroleum ether.

In another preferred embodiment, the microparticle phase contains microparticles and liquid incompatible with the oil phase liquid in the oil storage well; preferably, the microparticle phase is a non-organic phase; more preferably, the microparticle phase is an aqueous phase or a non-organic buffer.

In another preferred embodiment, the method for forming and exporting single-microparticle-encapsulated droplets further includes a sample detection step, wherein the sample detection step is carried out before step (iv), and the method used for the sample detection step is selected from, but not limited to, Raman spectral analysis, fluorescence detection, optical microscope detection, and conductance detection;

In another preferred embodiment, the method for exporting a droplet encapsulating a single target microparticle includes capillary tube exporting and pipette exporting;

In another preferred embodiment, the method for forming and exporting single-microparticle-encapsulated droplets further includes performing operations on the exported target microparticles, wherein the operations include single-cell sequencing, single-cell morphology analysis, and single-cell culturing.

In another preferred embodiment, the method for forming and exporting single-microparticle-encapsulated droplets includes the steps: (i) injecting an oil phase in an oil storage well, (ii) injecting a microparticle phase solution into a sample channel through an injection hole, and adjusting the height of a sample container on the height-adjustable sample holder to h0, so that the interface between the microparticle phase and the oil phase at the outlet is steadily stationary near the outlet of the sample channel, (iii) collecting the characteristic signal of single microparticles in the detection cell (5), and capturing the target microparticles with optical tweezers, moving the microfluidic chip and dragging the desired target microparticles near the interface between the aqueous phase and the oil phase, (iv) adjusting the height of the sample container on the height-adjustable sample holder to h, and pushing the microparticle and a part of the water to the oil phase by gravity, to form an water-in-oil droplet, and then adjusting the height of the sample container back to h0, so that the interface between the microparticle phase and the oil phase is stationary again near the outlet of the sample channel, (v) contacting the microparticle-encapsulated droplets by a capillary tube, as according to the characteristic of capillary force, making the droplets automatically enter the capillary tube with some oil, due to the capillary tube's good wetting effect.

In another preferred embodiment, the method for injecting the microparticle phase solution into the sample channel through the injection port is a static pressure injection method.

In another preferred embodiment, the method for collecting the characteristic signal of single microparticles in a sample channel is selected from Raman signal acquisition, fluorescence detection, and optical microscope detection; more preferably, the position for collecting the characteristic signal of a single microparticle is the detection cell.

In another preferred embodiment, the laser wavelength of the optical tweezers is 1064 nm.

In another aspect of the present invention, it provides uses of a microfluidic chip, a microfluidic chip device, or a microfluidic operating system, wherein the uses include single microparticle screening, formation of single microparticle-encapsulated droplets, or exportation of single microparticle-encapsulated droplets.

It should be understood that, within the scope of the present invention, the above technical features of the present invention and the technical features specifically described in the following (such as the Examples) may be combined with each other to form a new or preferred technical solution. Due to space limitations, they will not be repeated here.

This invention has the following technical advantages:

1. It is suitable for Raman detection and exportation of microparticles with various sizes, such as yeast cells of tens of microns and bacterial cells of about 1 micron.

2. Single cell selection, isolation and exportation are achieved, and the process has low impact on cell viability and can be successfully docked with downstream single cell sequencing.

3. The speed of single microparticle screening and moving is fast, and the operation time of moving single microparticle from the chip to the test tube is 1 to 2 minutes.

4. Chips can be reused, which reduces the operating costs.

5. Operation is easy.

DETAILED DESCRIPTION OF THE INVENTION

The microfluidic chip, the microfluidic chip device, the microfluidic operating system and the method for forming and exporting single microparticle-encapsulated droplets, provided by this invention, can be used to separate single microparticles from biological and non-biological sources, for example, the isolation of single particles of eukaryotic cells (such as animal cells, plant cells, fungal cells and so on), prokaryotic cells (such as bacterial cells, and so on), single cell organisms, virus particles, organelles, particles formed by biological macromolecules, drug particles, drug carrier particles, lipid of plastids, polymer particles, and other natural or synthetic particles.

The present invention will be further described below with reference to the specific examples. It should be understood that these examples are only intended to illustrate the present invention and not to limit the scope of the present invention. The experimental methods without detailed conditions in the following examples are generally performed according to conventional conditions, such as those described in Sambrook et al., Molecular Cloning: Laboratory Manual (New York: Cold Spring Harbor Laboratory Press, 1989), or according to the manufacturer suggested conditions. Unless stated otherwise, percentages and parts are by weight.

Example 1

1. Preparation of the Microfluidic Chip:

(i) A sample injection hole and a liquid storage well hole were punched in the upper layer of quartz glass by ultrasonic drilling, and the distance between the holes depended on the length of the channel. The upper layer of quartz glass was a smooth flat surface with a thickness of 0.5 to 1 mm and had no etched pattern. (The order of the upper and lower layers of quartz glass was determined by the optical path of the optical tweezers. Since the microscope used in this experiment was an upright microscope, wherein the optical tweezers passed through the chip from top to bottom, it was to be ensured that the upper surface of the chip was a smooth optical surface. Therefore, the upper layer was made of smooth quartz glass, and the quartz glass engraved with channels was on the lower layer.)

(ii) The surface of the lower quartz glass was etched according to the channel design, and the channel height was about 15-50 microns.

(iii) The two layers of glass were aligned and bonded with low-temperature bonding method.

(iv) Surfaces were treated by hydrophobization (using silylation reagent), to form a hydrophobic and lipophilic surface at the location of the oil storage well.

(v) For single microparticle-encapsulated droplets, the oil phase was mineral oil (containing 2% wt surfactant Span 80). Because the density of this oil phase is less than that of water, the generated droplets would be located at the outlet of the microchannel at the bottom of the oil storage well, which is convenient for observation and exportation.

Figure 1:
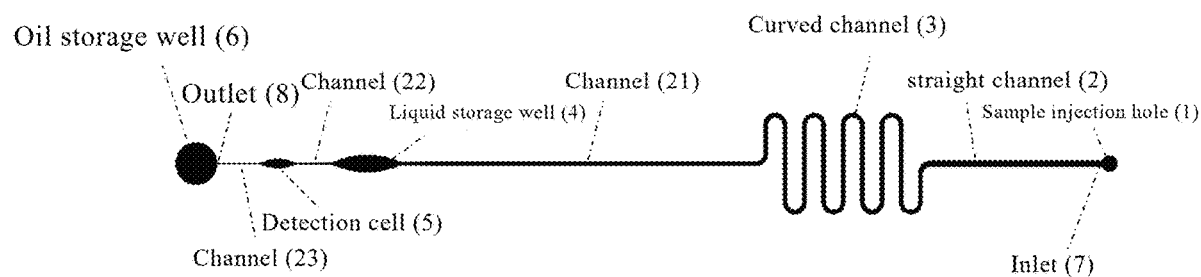
FIG. 1 shows a schematic diagram of microfluidic chip design.

The design schematic the microfluidic chip are shown in FIG. 1.

Figure 2:
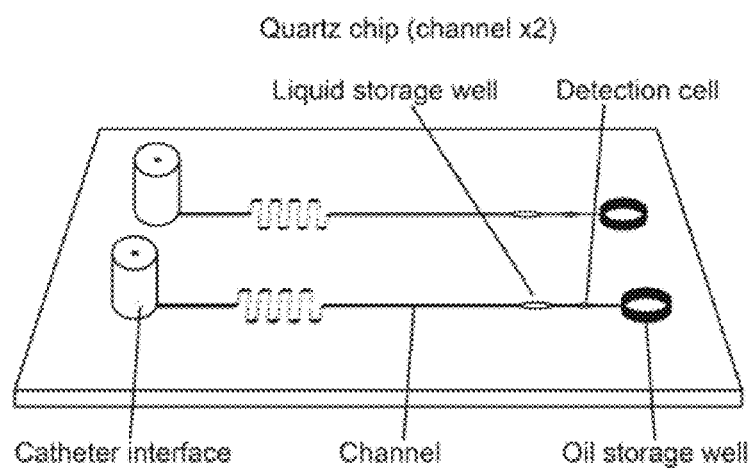
FIG. 2 shows a picture of a microfluidic chip.

2. Preparation of Microfluidic Chip Devices and Systems for Forming Single Microparticle-Encapsulated Droplets The liquid sample injection device selected here was a gravity-driven sample injection device. The sample container was suspended on a height-adjustable sample holder, and the sample container was connected with the sample injection hole on the microfluidic chip through a catheter. A schematic diagram of a microfluidic chip device consisting of a liquid sample injection device and a microfluidic chip is shown in FIG. 2A. When the microfluidic chip was placed on the microscope platform, the microfluidic chip device and the microparticle capturing device together constructed a microfluidic operating system for forming single microparticle-encapsulated droplets.

Example 2

Figure 3:
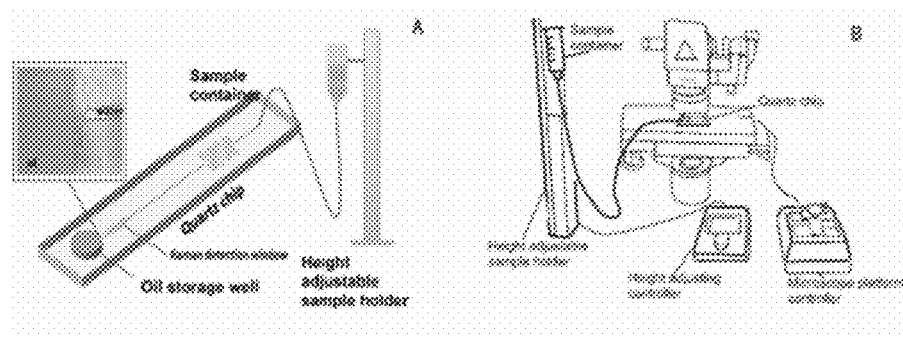
FIG. 3 shows a diagram of microfluidic chip device for forming single microparticle-encapsulated droplets. A shows a schematic diagram of a microfluidic chip device composed of a liquid sample injection device and a microfluidic chip. B shows a picture of a microfluidic operating system, which is composed of a microfluidic chip device and a microparticle capture device, and is used to form a single microparticle-encapsulated droplet.
Figure 4:
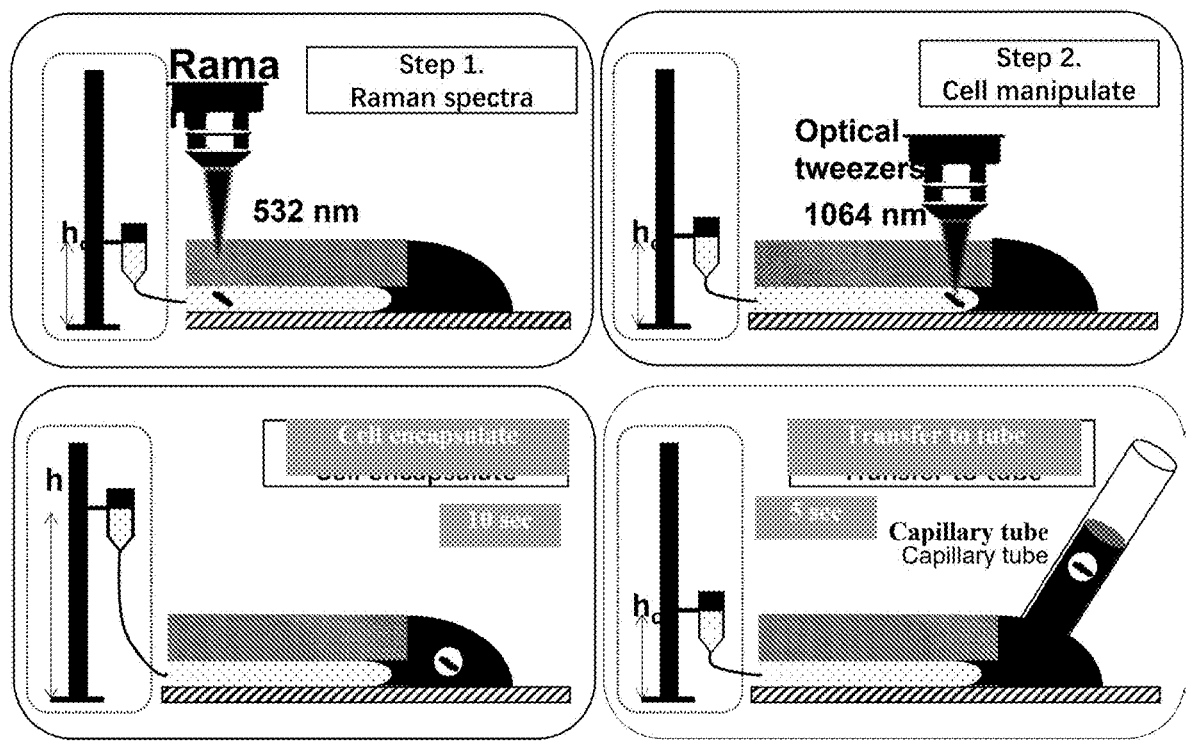
FIG. 4 shows the process of forming a single microparticle-encapsulated droplet.

The schematic figure of steps for formation and exportation of target single microparticle-encapsulated droplets is shown in FIG. 3.

(i) Oil phase (usually mineral oil containing surfactants) was injected into the oil storage well at the outlet of the sample channel.

(ii) Microparticle phase (cell phase in this example) solution was injected into the chip channel through the injection hole by static pressure injection method, and the height of the sample holder was adjusted to h0, so that the interface between the cell phase and the oil phase at the sample outlet was steadily stationary near the sample outlet.

(iii) The characteristic map (such as Raman spectrum, 532 nm laser) of single cells was collected in the detection cell, and the desired target cells were captured by optical tweezers (such as 1064 nm laser). The microfluidic chip was moved, so that the target cells were dragged to the vicinity of the interface between the aqueous phase and oil phase.

(iv) The height of the sample holder was adjusted to h, the cells and part of the water was pushed into the oil phase by gravity to form water-in-oil droplets, and then the height of the sample holder was adjusted back to h0, so that the interface between the cell liquid and the oil phase was stationary again near the outlet of the sample channel.

(v) The microparticle-encapsulated droplets were contacted by a capillary tube. Since the oil phase has good wetting effect on the capillary tube, the droplets automatically entered the capillary tube with part of the oil, due to capillary force. FIGS. 5A-F show that a single-cell-encapsulated droplet can be successfully exported by a capillary tube.

The height of the sample holder is determined by the internal fluid resistance of the quartz chip. According to the channel size of the quartz chip used and the height of the microscope platform, a 1-meter-high sample holder was selected for this experiment. The sample holder was designed as a slide rail that has an electrically movable slider for fixing the sample container, as shown in FIG. 3B.

Example 3

DNA amplification and electrophoresis were performed on the isolated single cells.

Figure 5:
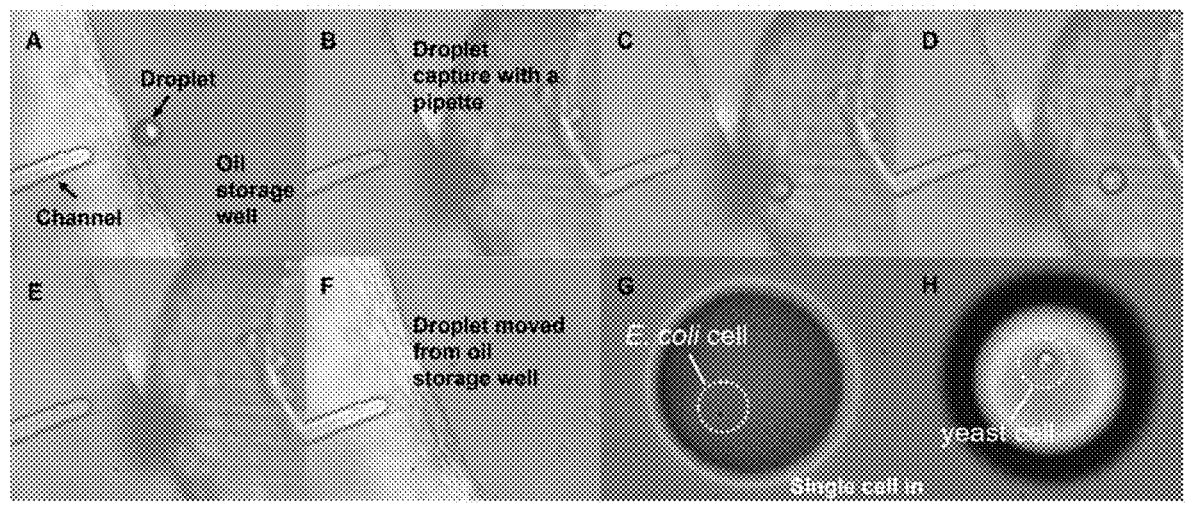
FIG. 5 illustrates the process of sorting individual cells by the microfluidic chip device has low impacts on cell viability. A shows a just wrapped droplet that is then sucked out of the open oil storage well by the capillary tube, the whole process of which does not require external power and is based on the capillary force of the oil phase in the capillary tube. B shows that by placing the capillary tube at the channel outlet, the oil phase will flow into the capillary tube by capillary force, and the single cell encapsulated droplets in the oil phase will then flow into the capillary tube along with the oil phase. C—F are video screenshots of this process. G and H are the cell encapsulated droplets under the field of view of the 50× objective lens, taking *E. coli* cell and yeast cell as model cells respectively, in which it is found that two cells of different sizes can be successfully encapsulated in the droplets and exported.

The droplets separated in Example 2 were observed under a 50× objective lens, and it was observed that the single cell was successfully wrapped in the droplet. This method is applicable to cells with different sizes, from about one micrometer to about tens of micrometers, as shown in FIG. 5G and FIG. 5H wherein the of *E. coli* cells and yeast cells were encapsulated in droplets using this method. Because the density of the mineral oil used in this method is less than that of the cell suspension (water), the droplets will automatically distribute at the bottom of the capillary tube during the droplet transferring process. Droplets can be exported by just contacting the wall of the test tube or centrifuge tube using the capillary tube containing the droplet, which makes the transferring process simpler and more convenient with higher success rate.

Figure 6:
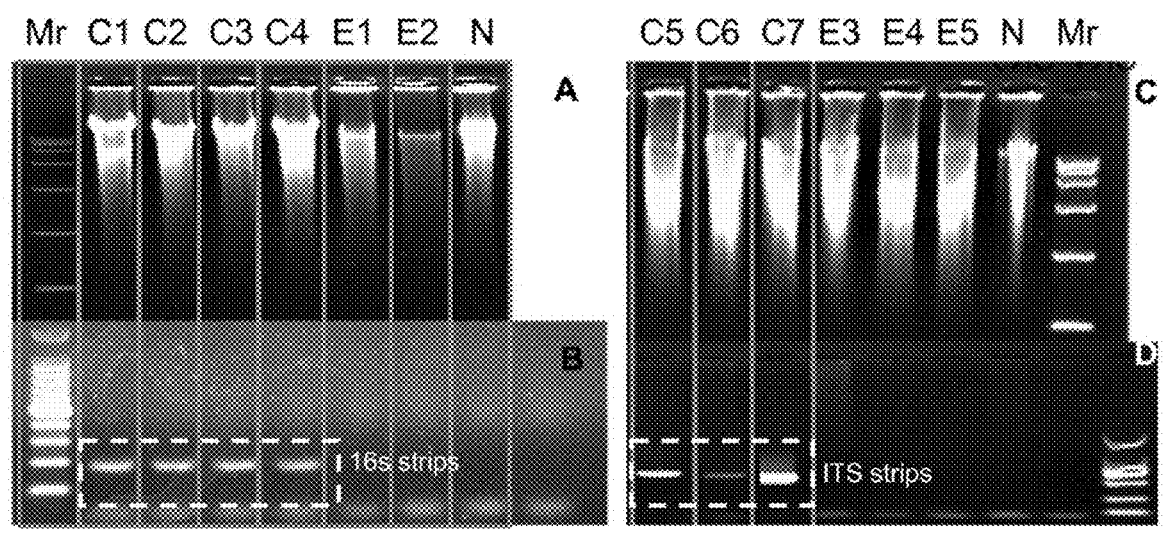
FIG. 6 shows the DNA amplification results. A and C show the MDA amplification results, and B and D show the 16S identification results, wherein N is the negative control of the MDA (multiple substitution) amplification. The experiment proved that the droplets can successfully encapsulate and export the cells, and the exported cells can be successfully used for downstream expansion and sequencing analysis.

The single cell encapsulated droplets in the capillary tube were centrifuged and introduced into a separate centrifuge tube, and the amplification substrate was added for DNA amplification, as shown in FIG. 6. In this test, *E. coli* (FIG. 6A and FIG. 6B) and yeast (FIG. 6C and FIG. 6D) were used as model cells, and some empty droplets were used as controls (E1 and E2 are *E. coli* sample control empty droplets, E3E4E5 are yeast control empty droplets). It was found that no amplification products appeared in the empty droplets, and that the single-cell-encapsulated droplets were successfully expanded, which proves that the cells isolated by this method can be successfully used for downstream analysis such as single-cell sequencing, and that pollution can be successfully avoided in the single cell screening process.

All documents mentioned in the present invention are incorporated by reference in this application, as if each document was individually incorporated by reference. In addition, it is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

The invention claimed is:

1. A method for forming and exporting single microparticle-encapsulated droplets, wherein the method utilizes a microfluidic chip, the microfluidic chip comprising: a cover layer and a substrate layer; wherein the substrate layer comprises at least one sample channel, and the at least one sample channel comprises a microfluidic channel and a detection cell; and the cover layer comprises a sample injection hole and an oil storage well hole;

wherein the oil storage well hole and the substrate layer form an oil storage well; an inlet of the at least one sample channel is fluidically connected with the sample injection hole, and an outlet of the at least one sample channel is fluidically connected with the oil storage well, wherein the detection cell and the oil storage well hole are connected through a straight channel, the method comprising: (i) injecting an oil phase into the oil storage well; (ii) injecting an aqueous phase containing a microparticle into the at least one sample channel of the microfluidic chip through the sample injection hole; (iii) adjusting liquid flow in the at least one sample channel so that an interface between the microparticle phase and the oil phase in the oil storage well is steadily stationary nearby the outlet of the at least one sample channel; (iv) capturing a target microparticle with the microparticle capture device, moving the microfluidic chip, so that the target microparticle is dragged to a vicinity of the interface between the aqueous phase and oil phase by optical tweezers; (v) adjusting liquid flow in the at least one sample channel to allow the target microparticle to enter the oil storage well and to form liquid droplets encapsulating a single target microparticle; and (iv) exporting the droplets encapsulating the single target microparticle; wherein a method for adjusting liquid flow in the at least one sample channel is selected from the group consisting of gravity-driven adjusting, injection pump-driven adjusting, and peristaltic pump-driven adjusting and combinations thereof, and a method for exporting the droplets encapsulating the single target microparticle is selected from the group consisting of capillary tube exporting, pipette exporting and combinations thereof.

2. A method for forming and exporting single microparticle-encapsulated droplets, wherein the method utilizes a microfluidic chip device for forming single microparticle-encapsulated liquid droplets, wherein the microfluidic chip device comprises a microfluidic chip and a liquid sample injection device;

wherein the microfluidic chip comprises: a cover layer and a substrate layer; wherein the substrate layer comprises at least one sample channel, and the at least one sample channel comprises a microfluidic channel and a detection cell; and the cover layer comprises a sample injection hole and an oil storage well hole; wherein the oil storage well hole and the substrate layer form an oil storage well; an inlet of the at least one sample channel is fluidically connected with the sample injection hole, and an outlet of the at least one sample channel is fluidically connected with the oil storage well, wherein the detection cell and the oil storage well hole are connected through a straight channel, and wherein the liquid sample injection device is connected with the sample injection hole via a catheter, and the liquid sample injection device is selected from the group consisting of a gravity-driven sample injection device, a syringe, a peristaltic pump, a syringe pump, and combinations thereof, and the method comprising: (i) injecting an oil phase into the oil storage well; (ii) injecting an aqueous phase containing a microparticle into the at least one sample channel of the microfluidic chip through the sample injection hole to form a microparticle phase; (iii) adjusting liquid flow in the at least one sample channel so that the interface between the microparticle phase and the oil phase in the oil storage well is steadily stationary nearby the outlet of the at least one sample channel; (iv) capturing a target microparticle with a microparticle capture device, moving the microfluidic chip, so that the target microparticle is dragged to a vicinity of the interface between the aqueous phase and oil phase by optical tweezers; (v) adjusting liquid flow in the at least one sample channel to allow the target microparticle to enter oil storage well and to form liquid droplets encapsulating a single target microparticle; and (iv) exporting the droplets encapsulating the single target microparticle;

wherein a method for adjusting liquid flow in the at least one sample channel is selected from the group consisting of gravity-driven adjusting, injection pump-driven adjusting, and peristaltic pump-driven adjusting and combinations thereof, and a method for exporting the droplets encapsulating the single target microparticle is selected from the group consisting of capillary tube exporting, pipette exporting and combinations thereof.

* * * * *